(12) United States Patent
Hammond

(10) Patent No.: US 6,460,702 B2
(45) Date of Patent: *Oct. 8, 2002

(54) FIRST AID KIT AND METHOD OF REPLENISHING

(75) Inventor: David A. Hammond, Tinton Falls, NJ (US)

(73) Assignee: DLH, Inc., Tinton Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/962,511

(22) Filed: Sep. 25, 2001

(65) Prior Publication Data

US 2002/0008047 A1 Jan. 24, 2002

Related U.S. Application Data

(63) Continuation of application No. 09/326,837, filed on Jun. 7, 1999, which is a continuation of application No. 09/009,216, filed on Jan. 20, 1998, now Pat. No. 5,931,304.

(51) Int. Cl.$^7$ ............................................. B65D 69/00
(52) U.S. Cl. .................... 206/570; 206/425; 206/459.5; 206/438
(58) Field of Search ................................. 206/570, 571, 206/572, 438, 459.5, 803, 425

(56) References Cited

U.S. PATENT DOCUMENTS 5,848,700 A * 12/1998 Horn ........................... 206/570
5,931,304 A * 8/1999 Hammond .................... 206/570

* cited by examiner

Primary Examiner—Luan K. Bui
Assistant Examiner—Jila M. Mohandesi
(74) Attorney, Agent, or Firm—Gardner, Carton & Douglas

(57) ABSTRACT

The first aid kit of the present invention includes a case (12), which includes a quick access to the contents carried by the case (12). The case (12) further provides, on the inside a plurality of compartments (37) arranged in sequence to obtain a card catalogue/file cabinet-like effect. Contained in the sequential compartments (37) are packs (40), which are specifically designed with products appropriate for a particular first aid situation. The first aid kit (10) further provides an instruction booklet (46) which contains detailed instructions regarding the products contained in each pack (40) as well as instructions on use of the products for different types of first aid situations. The first aid further includes an overview card (50) which is an overview of the components of the first aid kit (10), identifying each of the packs (40), for quick reference in a first aid situation. Finally, each of the packs (40) contains medical products specifically selected for different types of first aid situations as well as an instructional card (37) which gives quick reference instructions for administration of first aid in these situations.

10 Claims, 6 Drawing Sheets

FIRST AID KIT AND METHOD OF REPLENISHING

This is a Continuation Application of U.S. patent application Ser. No. 09/326,837 filed Jun. 7, 1999 that is, in turn, a Continuation Application of U.S. patent application Ser. No. 09/009,216, filed Jan. 20, 1998, now U.S. Pat. No. 5,931,304, Aug. 3, 1999.

FIELD OF THE INVENTION

The present invention relates in general to first aid kits and, in particular, to a first aid kit which is adaptable to a plurality of first aid environments.

BACKGROUND OF THE INVENTION

The use of kits containing a select number of products appropriate for use in first aid conditions is known in the art. Typically, such kits consist of a small container into which products predicted to be applicable to a wide variety of first aid situations are included. A drawback of such kits, however, is that certain supplies of medical products found in such kits typically are used up after addressing a single first aid condition. An additional drawback is that no clear cut product usage instructions or resupply directions are delineated for the user. Thus, often the user must purchase a new kit after each use for a first aid condition. This results in the wasteful accumulation of unused products provided in the kit but not utilized in the first aid condition.

In an effort to alleviate such waste, manufacturers have targeted first aid kits for different applications, such as for automobile travel, boating, camping, and the like. With these kits, medical supplies which are predicted to be more specifically suited for the types of injuries likely to occur in these environments are included. However, these specifically designed kits suffer from the same drawbacks in that, after one first aid situation is encountered, the kits are replaced.

What would thus be advantages would be for a first aid kit which was adapted for use in a wide variety of different types of first aid situations. Such a kit would also appeal to a diversity of users by ease in selection and usage of the supplies. Such a kit would appeal to a diversity of users by ease in selection and usage of the instructions. Such a kit would also enable the user to replenish the kit after a first aid situation is encountered without the need to buy a new kit. Such first aid kit would provide quick access to the appropriate medical product for a given type of first aid condition. Such kit would further provide quick access to information regarding different first aid situations so that the users could appropriate and properly use the supplies found in the kit.

SUMMARY OF THE INVENTION

The present invention provides a first aid kit which is adapted for use in a wide variety of different types of first aid situations. The present invention provides a first aid kit which appeals to a diversity of users by ease in selection and usage of the supplies. The present invention provides a first aid kit which appeals to a diversity of users by ease in selection and usage of the instructions. The present invention provides a first aid kit which also enables the user to replenish the kit after a first aid situation is encountered without the need to buy a new kit. The present invention provides a first aid kit which allows quick access to the appropriate medical product for a given type of first aid condition. The present invention provides a first aid kit which allows quick access to information regarding different first aid situations so that the users can appropriate and properly use the products.

The first aid kit of the present invention includes a carrying case which includes means for providing quick access to the contents carried by the case. The carrying case further provides, on the inside, a plurality of compartments arranged in sequence to obtain a card catalogue/file cabinet-like effect. Contained in the sequential compartments are first aid packs which are specifically designed with products and instructions appropriate for a particular first aid situation. The first aid kit further provides an instruction booklet which contains detailed instructions regarding the products contained in each pack as well as instructions on use of the products for different types of first aid situations. The first aid kit further includes an overview card which includes an overview of the components of the first aid kit, identifying each of the packs, for quick reference in a first aid condition. Finally, each of the packs contains medical products specifically selected for different types of first aid situations as well as an instructional card which gives quick reference instructions for administration of assistance in these situations.

In the preferred embodiment of the present invention, each of the packs is designated a color for a first aid situation which is different than the colors designated for other first aid situations. Additionally, the guidebook is color coordinated with the packs such that the detailed first aid instructions are found on pages which have borders matching the color of the pack. Finally, the overview card is likewise color coordinated to assist the user in quickly finding the appropriate pack for the type of first aid situation encountered.

In still a further preferred embodiment, in addition to color coordinating the packs, each pack is designated by a unique icon which is recognizable in any language. Again, the icons are utilized within the detailed guidebook as well as the first aid kit overview. Additionally, the instructional cards contained in the packs as well as the detailed instructions contained in the guidebook are set forth in graphical depictions to guide the user in the use of the medical products in the type of first aid situation encountered.

DETAILED DESCRIPTION OF THE PREFERRED EMBODIMENT

Figure 1:
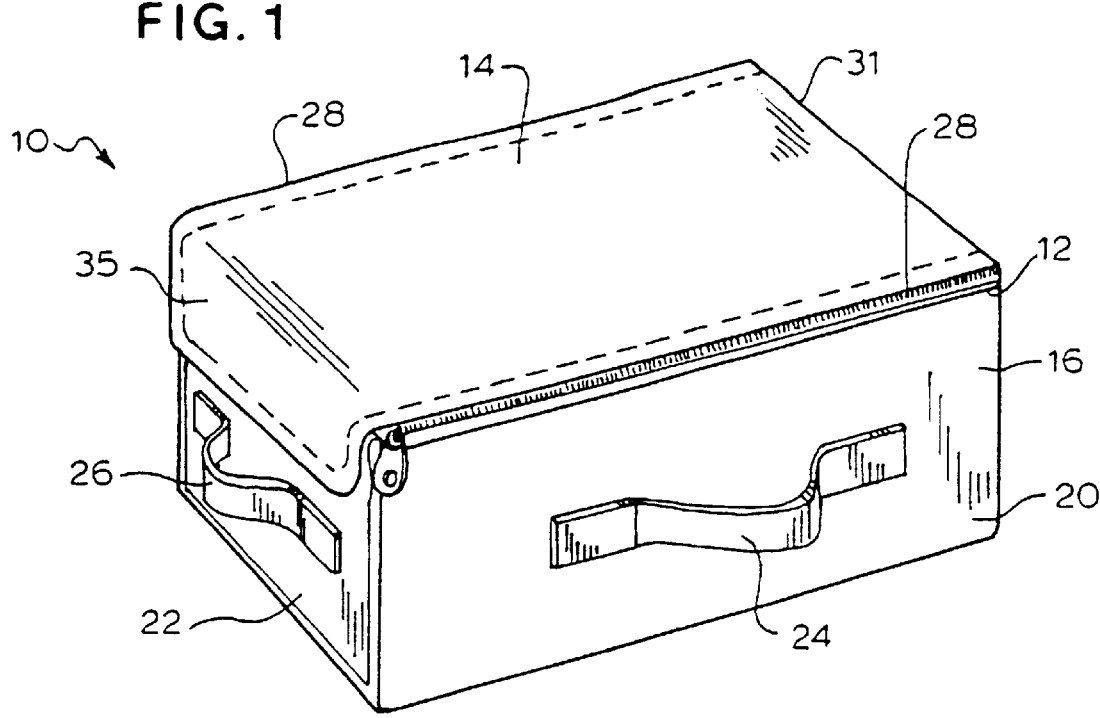
FIG. 1 is a perspective view of a first aid kit made in accordance with the principles of the present invention.

Referring first to FIG. 1, a perspective view of a first aid kit 10 made in accordance with the principles of the present invention is seen. The first aid kit 10 is carried in a case 12 which has a top 14 and a base 16 having a bottom, two sides 20, and two ends 22. The sides 20 of the base 16 are generally rectangular and the ends 22 of the base 16 are generally square. The first aid kit 10 of the present invention is preferably made of a lightweight material to enable ease of carrying. In the preferred embodiment, the first aid kit 10 is made of a flexible material such as nylon. In an alternative preferred embodiment, the kit 10 can be made of a rigid, lightweight material such as plastic.

To further aid in carrying, the first aid kit 10 is provided with a handle 24. In the preferred embodiment, a handle 24 is provided on a side which enables the user to carry the first aid kit in a generally horizontal orientation. Additionally, a handle 26 can be provided on the end of the first aid kit which enables the user to carry the first aid kit in a vertical orientation. Alternatively, a shoulder strap (not shown) can be provided alone or in combination with a handle.

Figure 2:
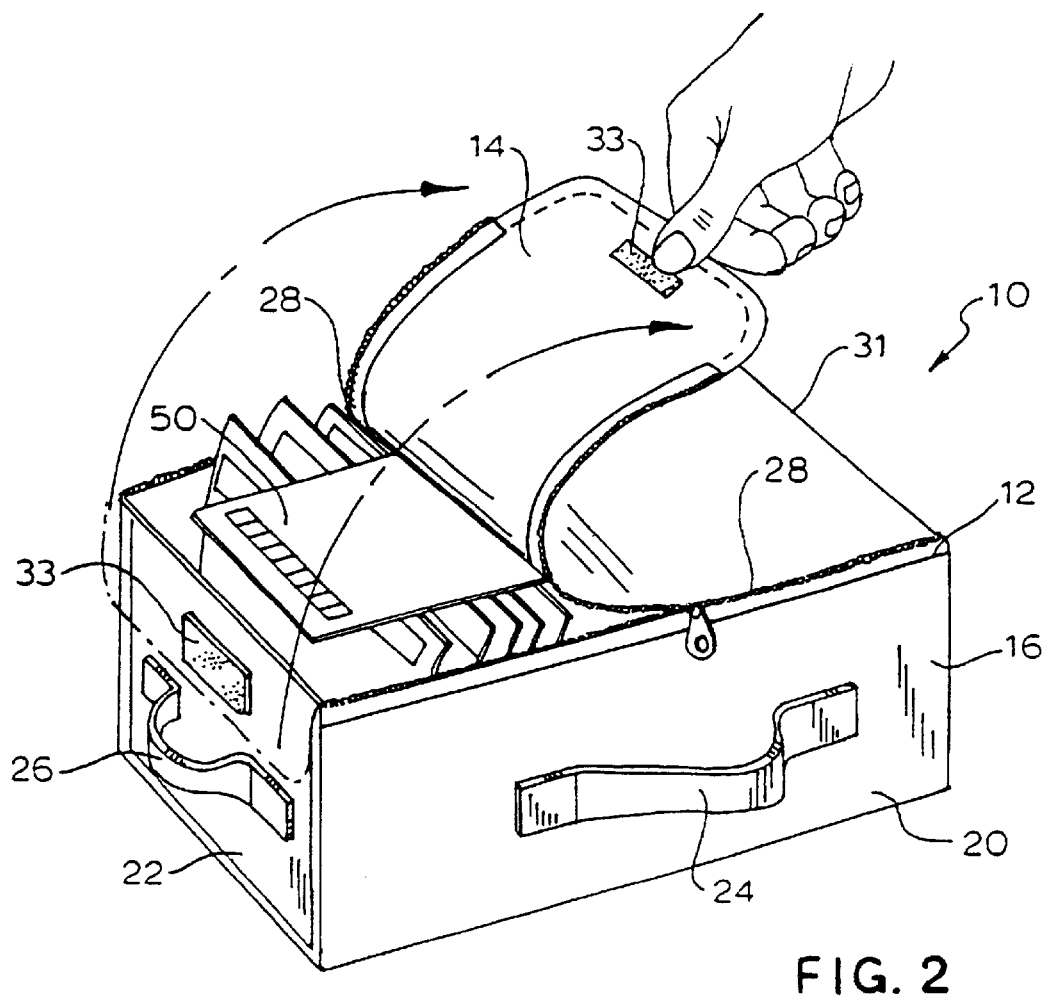
FIG. 2 is a perspective view of the first aid kit of FIG. 1 showing a user opening the first aid kit for access to the contents.

The top 14 is secured to the base 16 by use of a closure means for enabling quick access to the contents of the first aid kit 10. In a preferred embodiment, the closure means consist of a pair of zippers 28 which secure the top 14 to the sides 20. A first end of the top 14 is secured to the base by a living hinge 31 integrally formed with that end of the base 16. The end of the top 14 opposite the living hinge 31 is secured to the base 16 by a hook and loop style fastener 33 contained on an over-flap 35. Thus, in use, a user simply pulls the over-flap 35 over the top 14 thereby releasing the hook and loop fastener 33. On further pressure upward and rearward, the zippers 28 are automatically opened thus provided quick access to the content of the first aid kit 10, as seen in FIG. 2.

Figure 3:
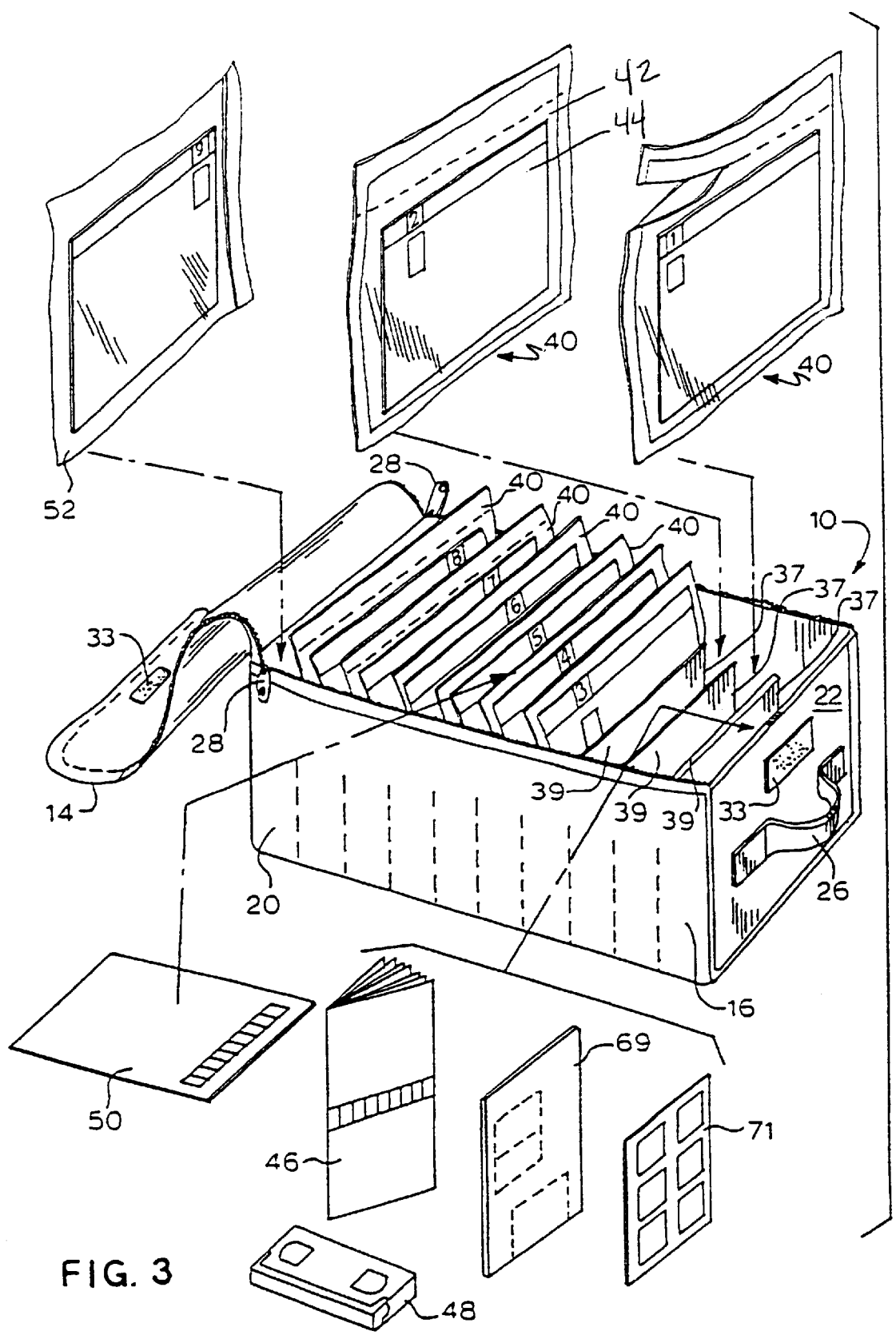
FIG. 3 is an exploded view of the contents and orientation of a first aid kit made in accordance with the principles of the present invention.

Referring to FIG. 3, the base 16 of the first aid kit 10 defines a plurality of compartments 37. Each compartment 37 is sequentially oriented in front of the subsequent compartment. By so orienting the compartments 37 in this manner, a card catalogue/file cabinet like effect is provided in which contents can be carried in each compartment 37 in an easy to identify, upright position. Additionally, in each of the compartments 37, flexible walls 39 are used such that contents of different thicknesses can fit into each of the compartments 37.

The contents of the first aid kit 10 include a plurality of packs 40. Each of the packs 40 consist of a plastic bag 42, an instructional card 44, and a plurality of medical supplies provided for specific types of first aid situations. The first aid kit 10 further contains a detailed guidebook 46 which explains the use of the medical products in different types of first aid situations. In a further preferred embodiment, the first aid kit 10 contains an instructional video 48 which helps train the user on the use of the first aid kit 10. A card 50 is provided which contains an overview of the first aid kit 10.

Figure 7:
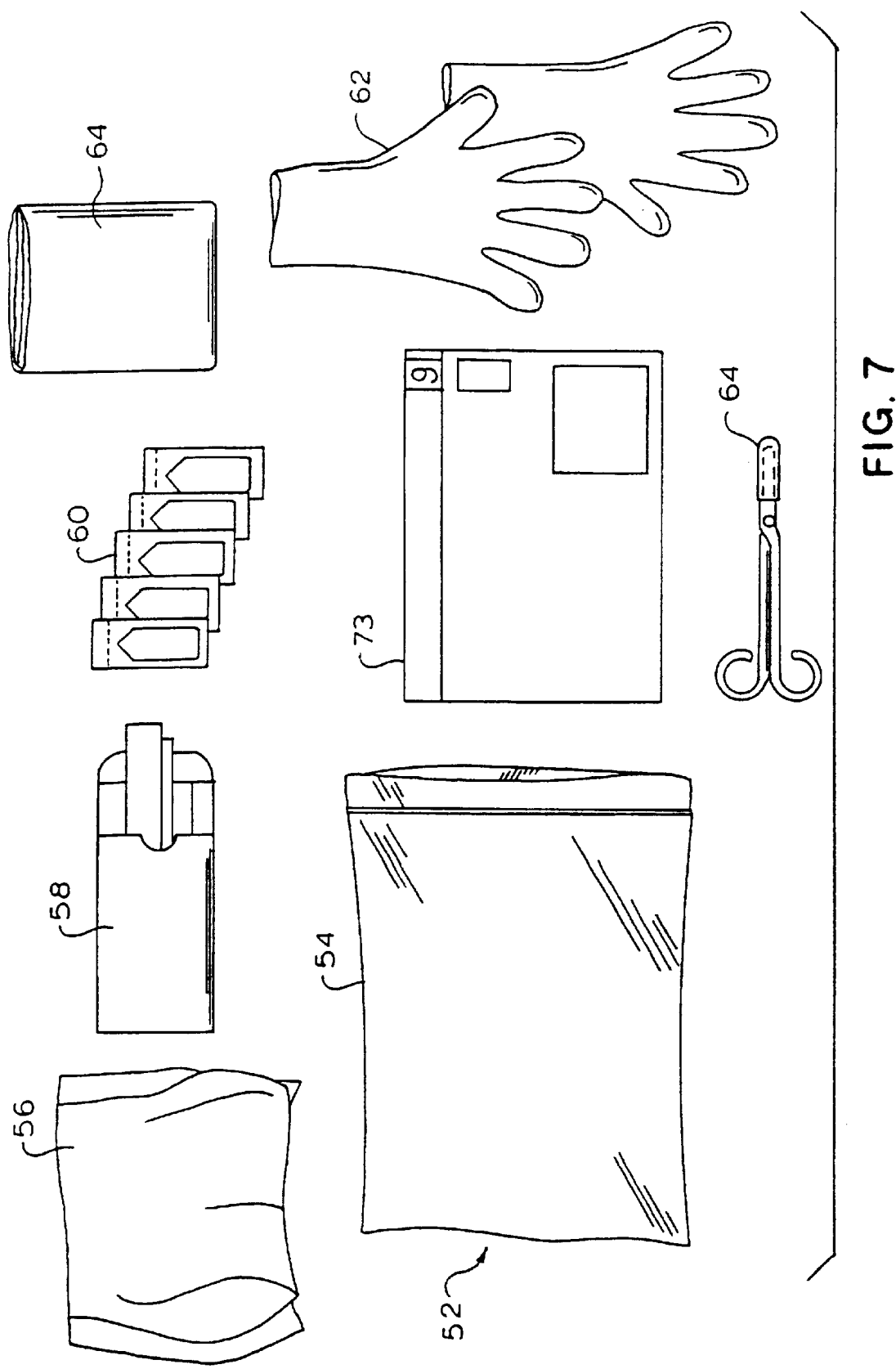
FIG. 7 is an exploded view of the extras pack of the first aid kit of FIG. 1.

In addition to the individual packs targeted for different types of first aid situations, as seen in FIG. 7, an extras pack 52 can be provided. The extras pack 52 includes a resealable container 54 which allows the user to store additional medical product supplies which are useful in a variety of first aid situations, such as, for example, an ice pack 56, bandages 58, ointment 60, disposable gloves 62, scissors 64, and a disposal bag 66. The user can add to the extras pack 52 user specific medical products such as, for example, asthmatic medicine for asthma sufferers, pain medication and the like.

The first aid kit further contains a magnetic card 69, which includes magnetic identifiers, a locator for the first aid kit, and a card having background medical information regarding family members. Further, a plurality of self-adhesive identifiers 71 are provided which can be placed in various locations, such as in kitchen cabinets, bathroom cabinets and the like, to quickly identify where the first aid kit 10 is stored. Still further, the guidebook 46 contains a page for the user to fill in information about emergency numbers and particular family health conditions.

The packs 40 contain specific medical supplies designed for specific types of first aid situations. In the preferred embodiment described herein, the different first aid situations include breathing, bleeding, shock, head and spine, bone, eye, burn and bites and stings. An instructional card 73 is provided for each of the different types of packs. The instructional card 73 for each pack 40 is color coordinated in a color unique to and different from the colors for the remaining packs 40. In addition, the overview card 50 utilizes these colors to identify the different packs 40 and the guidebook 46 sets forth the instructions for each of the different types of procedures based on pages which are bordered in a coordinated color.

For example, in the preferred embodiment described herein, a breathing pack is coordinated with the color blue, the bleeding pack is coordinated with the color red, the shock pack is coordinated with the color gold, the head and spine pack is coordinated with the color teal, the bone pack is coordinated with the color brown, the eye pack is coordinated with the color navy blue, the burn pack is coordinated with orange, the bite and sting pack is coordinated with the color magenta, and the extras pack is coordinated with the color grey. In addition, the guidebook 46 contains instructions for first aid conditions in which specific medical products are not used, such as, for example cardiopulmonary resuscitation (CPR). In the preferred embodiment, the CPR instructions are color coordinated purple. Additional instructions in the guidebook 46 include what to do if poison is ingested. The poison is color coordinated as green. In an alternative preferred embodiment, the packs 40 contained in the compartments 37 include, in sequential order, instructional cards for CPR and poison.

In addition the color coordination, the packs 40, guidebook 46 and overview card 50 employ icons for each of the first aid situations addressed. Thus, the icon for the breathing pack is a graphic depiction of the breathing channels in a human, the icon for the bleeding pack is a drop of blood, the icon for the shock pack is starburst, the icon for the head and spine pack is a human head, the icon for the bone pack is a broken bone, the icon for the eye pack is an eye, the icon for the burn pack is a flame, the icon for the bites and stings pack is a bee, and the icon for the extras pack is a medical bag. In addition, the guidebook 46 and instructional card 73 for CPR include an icon which is an electrocardiogram line while the guidebook 46 and instructional card 73 for the poison include an icon which is a skull and crossbones.

Figure 4:
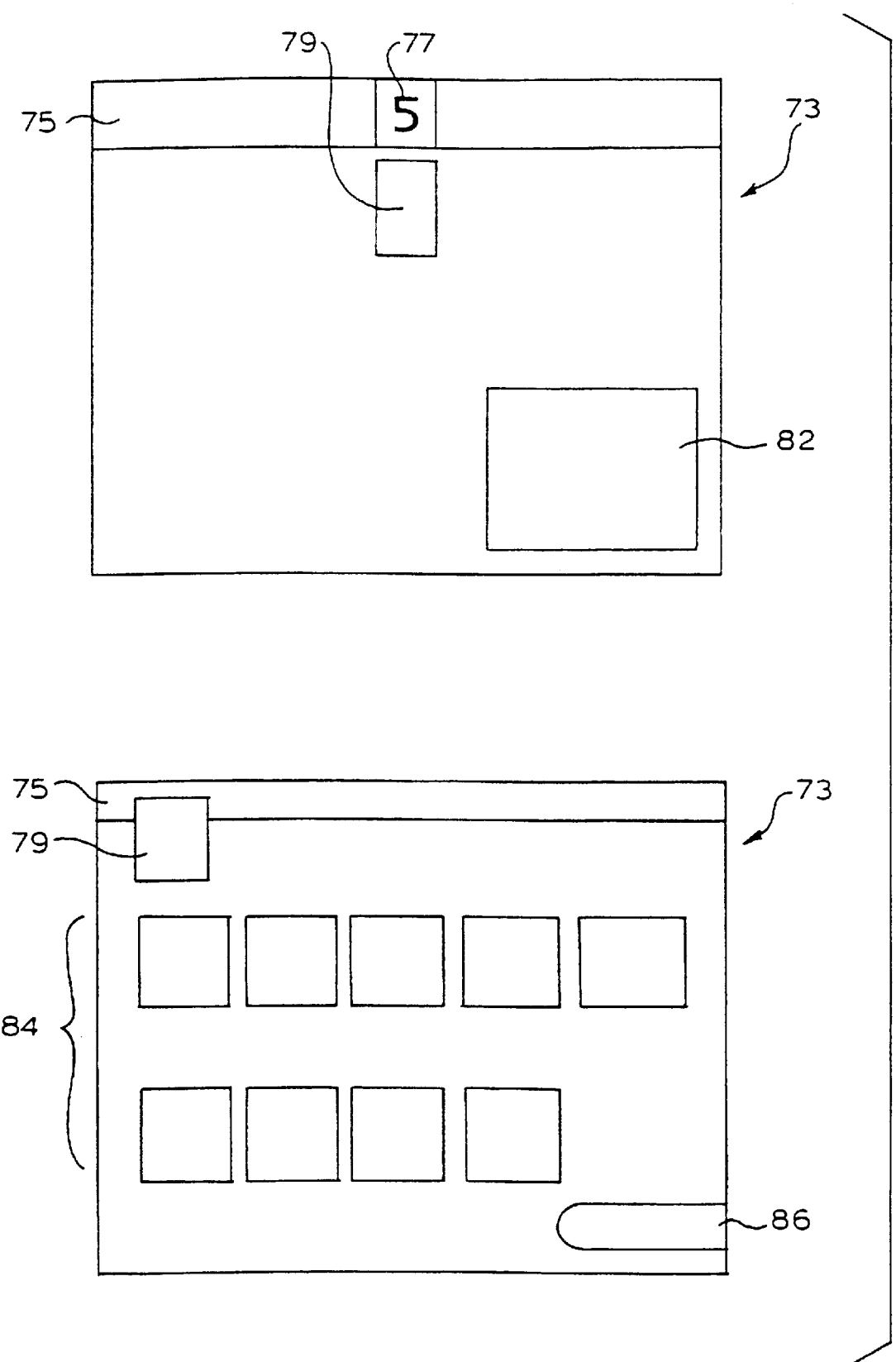
FIG. 4 is an exemplary card made in accordance with the principles of the present invention.

It is a particular advantage of the present invention that the instructional cards 73 for each pack are oriented with information in the same area of the card 73. Thus, once familiarized with the first aid kit 10, the user knows where to find appropriate information on any of the cards 73. Referring to FIG. 4, an exemplary instructional card 73 is seen which is made in accordance with the principles of the present invention. The upper edge of the card, which is visible to user when the pack is carried in the card catalogue/ file cabinet type orientation of the carrying case, sets out an identification of the type of pack on a band 75 of the coordinated color. The sequential number 77 of the pack 40 is also identified so that if the user is colorblind, the user can easily recognize, as well as replace and reorder the packs 40 as explained in detail below. The sequential numbers 77 are offset from each other, as seen in FIG. 3, to further enhance to the card catalogue/file cabinet like effect. Additionally, positioned underneath the band of color coordination 75 is the icon 79 for the particular pack 40. In the lower right portion of the front side of the card is an inventory 82 of the medical products in the pack 40.

Contained on the opposite side of the card 73 are instructions for use of the products contained in the pack 40. Again, along the upper edge of the card visible to the user when in the carrying case is a band of the coordinated color 75. Also positioned in the upper left-hand corner of the backside of the card is the icon 79. Positioned underneath the color coordinated band 75 is a series of step-by-step instructions 84, including a series of graphical instructions, on using the contents of the pack 40 in the care of the injured party. Positioned in the lower right-hand corner of the instructional card 86 is a toll-free number to call to reorder the pack 40, as explained in more detail below.

Utilizing this format, the packs 40 include contents directed toward specific first aid situations, as well as instructional cards 73 to direct the user how to use the products to care for the injured patient. In order to use one of the packs 40, the user opens the pack 40 along a tear line 88 which is provided on the pack 40. The pack 40 is provided sealed to maintain the sterility of the contents of the pack 40 while the tear line 88 allows the user easy access to the pack 40. In the preferred embodiment described herein, the tear line 88 is made according to the description provided in U.S. Pat. No. Re. 30,726, the disclosure of which is incorporated herein.

Figure 5:
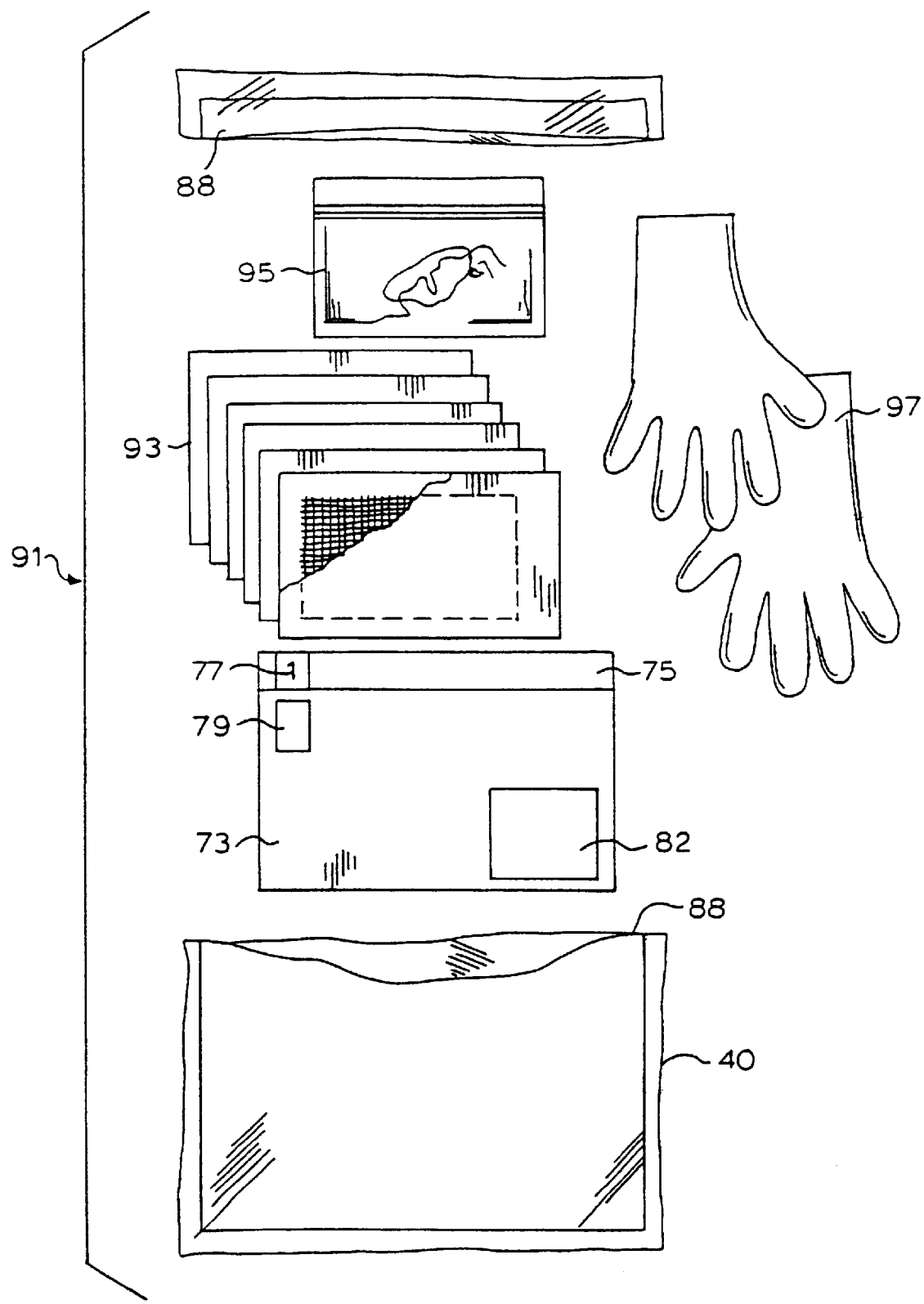
FIG. 5 is an exploded view of one of the packs of the first aid kit of FIG. 1.

Referring to FIG. 5, the breathing pack 91 is depicted as an exemplary example of the packs 40. The breathing pack 91 includes gauze sponges 93 which are used to clean fluid, saliva, etc. from around the mouth; a mouth guard 95 to allow for mouth-to-mouth resuscitation while avoiding mouth-to-mouth contact; and disposable medical gloves 97 to reduce contact with body fluids. The bleeding pack includes gauze sponges to control bleeding, a rolled bandage to hold gauze in place, cloth tape to hold the bandages and gauze in place, larger bandages which are used in combination with the bandages on larger wounds and disposable medical gloves to reduce contact with body fluids. The shock pack includes a thermal blanket. The head and spine pack include gauze sponges to control bleeding, a rolled bandage to hold the gauze in place, cloth tape to hold bandages in place, and disposable gloves to reduce contact with body fluids.

Figure 6:
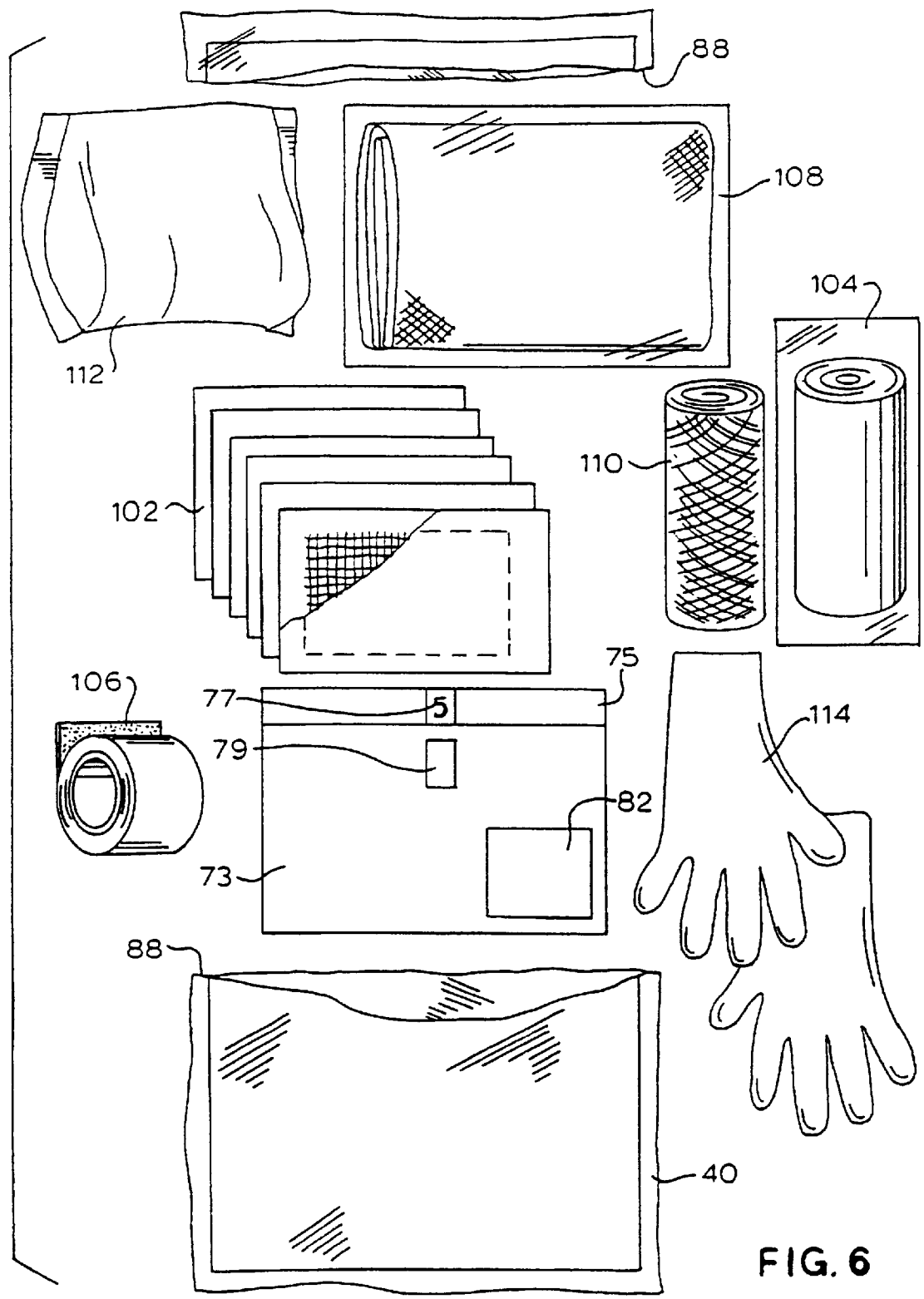
FIG. 6 is an exploded view of another of the packs of the first aid kit of FIG. 1.

Referring to FIG. 6, the bone pack 100 is depicted as a further exemplary example of the packs 40. The bone pack includes gauze sponges 102 which are used to control bleeding, rolled bandage 104 used to secure the splint and to hold the gauze in place, cloth tape 106 used to hold the gauze and splint in place, triangular bandage 108 used to make a sling to support a broken arm around the neck, wire splint 110 used to splint the injury, ice pack 112 used to reduce swelling and pain, and gloves 114 used to minimize contact with body fluids. The eye kit includes an eyewash solution to rinse the eyes, rolled bandage to hold an eye pad in place on the eyes, eye pads which are placed directly over the eyes, paper tape used to hold the eye pads and bandage in place, an ice pack which is used to reduce swelling and pain, and disposable medical gloves to reduce contact with body fluids. The burn pack includes gauze sponges to place on burns, rolled bandage to hold the gauze in place, cloth tape to hold the bandages and gauze in place, and gloves for use to reduce contact with body fluids. The bites and sting pack includes gauze bandages used to control bleeding, cloth tape to hold bandages in place, an ice pack used to reduce swelling and pain, alcohol pads to clean wound areas, tweezers to remove embedded insect parts, and disposable gloves to reduce contact with body fluids.

It is particular advantage of the present invention that once the particular pack 40 is used to address a first aid situation, the entire first aid kit 10 does not have to be replaced. In particular, the present invention includes a method of stocking and refurbishing packs 40. The kit 10 can be ordered as a standard, general purpose first aid kit. In an alternative preferred embodiment, the user can order different types of packs 40 within a kit 10 to address specific first aid situations. For example, user may equip the first aid kit 10 with packs 40 containing the types of injuries that are commonly associated with automobile accidents. Alternatively, the user can equip the first aid kit 10 with packs 40 particularly suited for boating accidents, camping accidents, and the like. After use of one of the packs 40, the user simply calls a toll-free number, specifies the type of pack 40 that has been used and reorders the pack 40 to again complete the first aid kit.

It should be understood that various changes and modifications preferred in to the embodiment described herein will be apparent to those skilled in the art. Such changes and modifications can be made without departing from the spirit and scope of the present invention and without demising its attendance advantages. It is therefore intended that such changes and modifications be covered by the appended claims.

What is claimed is:

1. A first aid kit comprising:

a carrying case defining an interior which includes means for providing quick access to the interior, the carrying case having a plurality of compartments in a card catalogue/file cabinet-like array;

a plurality of packs, each pack containing first aid products for different types of first aid situations, each pack containing more than one type of first aid product, and a plurality of packs containing a first aid product that is at least partially duplicative of the first aid product of another pack;

the plurality of packs having a similar shape, length and width and having variable thicknesses, the packs being sized and shaped to fit into the compartments of the carrying case; and an instructional card bearing an identification of the type of pack within each pack and bearing instructions for use of the contents within the pack for the first aid situation described on the identification.

2. The first aid kit of claim 1 further wherein the instructional card in the pack is designated a color which is different than the colors designated to the remaining instructional cards and packs.

3. The first aid kit of claim 2 further comprising a guidebook, the guidebook includes instructions regarding the products contained in each pack, the guidebook is color coordinated with the packs such that the instructions which correspond to the products appropriate for a particular first aid situation of a pack are found on pages of the guidebook which have a matching color to the pack.

4. The first aid kit of claim 3 further wherein the instructions contained in the guidebook are set forth in graphical depictions to guide the user in the use of the first aid products.

5. The first aid kit of claim 1 further wherein the instructional card is designated by an icon which is different than the icons designated to the remaining instructional cards and packs.

6. The first aid kit of claim 5 further comprising a guidebook, the guidebook includes instructions regarding the products contained in each pack, the guidebook is icon coordinated with the packs such that the instructions which correspond to the products appropriate for a particular first aid situation of a pack are found on pages of the guidebook which have a matching icon.

7. The first aid kit of claim 6 further wherein the instructions contained in the guidebook are set forth in graphical depictions to guide the user in the use of the first aid products.

8. The first aid kit of claim 1 further wherein the instructional cards within each pack are set forth in graphical depictions to guide the user in the use of the first aid products.

9. The first aid kit of claim 1 wherein the quick access means comprises a pair of zippers and a hook and loop fastener.

10. The first aid kit of claim 1 wherein the products for the management of first aid situations are selected from the group consisting of products for the management of a breathing first aid situation, products for the management of a bleeding first aid situation, products for the management of a shock first aid situation, products for the management of a head and spine first aid situations, products for the management of bone first aid situations, products for the management of burn first aid situations, products for the management of eye first aid situations, products for the management of bites and stings first aid situations, and combinations thereof.

* * * * *